US006466691B1

(12) United States Patent
Heuft

(10) Patent No.: US 6,466,691 B1
(45) Date of Patent: Oct. 15, 2002

(54) METHOD FOR TESTING THE RELIABILITY OF A TESTING APPARATUS, SPECIALLY AN EMPTY BOTTLE INSPECTING DEVICE

(75) Inventor: Bernhard Heuft, Burgbrohl (DE)

(73) Assignee: Heuft Systemetechnik GmbH, Burgbrohl (DE)

( * ) Notice: Subject to any disclaimer, the term of this patent is extended or adjusted under 35 U.S.C. 154(b) by 0 days.

(21) Appl. No.: 09/297,914

(22) PCT Filed: Nov. 12, 1997

(86) PCT No.: PCT/EP97/06310

§ 371 (c)(1),
(2), (4) Date: May 7, 1999

(87) PCT Pub. No.: WO98/21567

PCT Pub. Date: May 22, 1998

(30) Foreign Application Priority Data

Nov. 12, 1996 (DE) .......................................... 196 46 678

(51) Int. Cl.[7] .................................................. G06R 9/00
(52) U.S. Cl. .................... 382/142; 348/127; 250/223 B
(58) Field of Search ................................ 382/100, 141, 382/142, 143; 250/223 B; 356/237.1, 239.1, 239.4, 239.5, 240.1; 348/125, 127

(56) References Cited

U.S. PATENT DOCUMENTS 4,691,231 A    9/1987   Fitzmorris et al.
5,046,111 A  * 9/1991   Cox et al. .................... 382/143
5,734,467 A  * 3/1998   Lucas ....................... 356/240.1

FOREIGN PATENT DOCUMENTS

| DE | 3145832 A1 | 9/1982 | .......... G01M/13/00 |
| DE | 3324449 A1 | 1/1985 | .......... G01M/19/00 |
| DE | 3530903 A1 | 3/1987 | .......... G01B/21/02 |
| DE | 3208976 C2 | 3/1990 | ............ C03B/9/41 |
| DE | 3938471 A1 | 5/1991 | .......... G01N/21/84 |
| DE | 4113583 A1 | 10/1991 | ........... G07C/3/14 |
| DE | 4302656 C1 | 5/1994 | .......... G01M/19/00 |
| EP | 0382466 A2 | 8/1990 | .......... G01N/21/88 |
| JP | 03188308 | 8/1991 | .......... G01B/15/00 |

OTHER PUBLICATIONS

"Image Processing And Understanding For Automatic Inspection" West et al.; Trans Inst. M C vol. 10, No. 5; Oct.–Dec. 1988.

* cited by examiner

*Primary Examiner*—Joseph Mancuso
*Assistant Examiner*—Vikkram Bali
(74) *Attorney, Agent, or Firm*—Gardner Carton & Douglas

(57) ABSTRACT

To test the reliability of a testing apparatus which tests a large number of objects of the same type for one feature by generating a feature signal for each object and checking the feature signal for fulfilment of a first condition, a test signal is derived from the feature signals of several objects and the test signal is checked for fulfilment of a second condition. When checking if the test signal fulfils the second condition, the test signal can be compared with a reference value. The test signal can be the average of the feature signals of several objects.

5 Claims, No Drawings

METHOD FOR TESTING THE RELIABILITY OF A TESTING APPARATUS, SPECIALLY AN EMPTY BOTTLE INSPECTING DEVICE

BACKGROUND OF THE INVENTION

The invention relates to a method for testing the reliability of a testing apparatus which checks a large number of objects of the same type for one feature by generating a feature signal for each object and checking the feature signal for fulfilment of a first condition.

The fact that in the process, a feature signal fulfils a first condition can mean that the feature signal lies above or below a threshold value for this feature, or within a range formed by an upper and a lower limit value.

According to the state of the art, the procedure in reliability tests for testing apparatuses e.g. those for empty drinks bottles, so-called empty bottle inspectors, is that a row of test bottles is prepared so that each contains a certain defect according to the defect recognition specification, i.e. does not fulfil a certain feature. A special test bottle is prepared for every feature checked. The batch of test bottles is then incorporated in the stream of bottles at certain time intervals, e.g. every half hour, or after a certain number of bottles, e.g. 50,000 bottles. This operation can be automatic or manual. The test bottles are marked so that they are instantly recognisable as test bottles. The reliability test consists of checking whether these test bottles can be recognised as defective by the testing apparatus, for example the empty bottle inspector. In the method used up until now, the second condition is thus complementary to the first condition, i.e. the second condition is fulfilled in the test bottles if the test apparatus recognises that the test bottle is defective, i.e. that the first condition is not fulfilled. A record is kept in the testing apparatus. If the reliability test fails, i.e. if one or more of the test bottles is not recognised as defective, the test must be repeated. This is to ensure the operational dependability, i.e. the reliability, of a testing apparatus. This reliability test is unsatisfactory as it is only subsequently recognised that a testing apparatus has no longer functional reliably. The reasons for the failure of a testing apparatus are usually a dirty lens system or a failure of individual components of the recognition electronics.

With the method according to the state of the art, a large number of test bottles had to be used to test the reliability for example of an empty-bottle inspector, every test bottle having a single defect, e.g. a defective closure thread or a foreign body in a single recognition zone. Every type of defect and every recognition zone thus required its own specially prepared test bottle. If a test bottle had revealed several defects, the fact that this bottle was singled out would not have ensured that all the defects were recognized. A set of test bottles therefore consists of e.g. some 10 to 15 bottles.

SUMMARY OF THE INVENTION

The object of the invention is to create a method whereby a deterioration in the operating performance of a testing apparatus can be recognised as early as possible.

According to the invention, this object is achieved in that a signal is derived from the feature signals of several objects and the test signal is checked for compliance with a second condition.

Checking compliance with the second condition means that the test signal is compared with a reference value for the relevant feature. The reference value is typically the value to be expected for defect-free objects.

DETAILED DESCRIPTION OF THE INVENTION

The idea on which the invention is based is that the feature signals derived from the individual objects are observed over an extended period and a statement is made from the feature signals of a considerable number of checked objects about the reliability of the mode of operation of the testing apparatus. If it is shown e.g. that the feature signals have a tendency towards higher or lower values than the value to be expected with defect-free objects, this can be taken as a sign that the testing apparatus is not functioning properly.

The test signal can be the average of the feature signals of several objects. Because normally a very large number of objects pass through the testing apparatus within a short time, an average with a narrow scatter can be established, so that individual objects recognized as defective do not count. Preferably, during averaging, those objects in which the feature signal has not fulfilled the first condition, i.e., have been recognized as defective are furthermore not taken into account. The permitted upward or downward deviation of the test signal from the value to be expected with defect-free objects, the reference value, can be smaller than the deviation which is still acceptable for a single object, i.e. in which the first condition is still fulfilled.

The setting of the reference values for a testing apparatus can be carried out manually, e.g. on a keyboard, or by means of defect-free objects, the object being sent through the testing apparatus and the average of the feature signals thereby ascertained stored as a reference value. By means of the objects being sent through the testing apparatus several times more, the percentage reproducibility of the reference value can also be determined and the maximum permissible deviation of the test signal above or below the reference value specified, at which the second condition can still be seen as fulfilled.

The method according to the invention is of importance in particular in the food industry, as it is particularly important here that testing apparatuses operate error-free and that a reduction in the reliability of a testing apparatus is recognized before defective containers, e.g. empty bottles with foreign bodies such as dirt or cellophane films, with splinters on the edge of the opening or with caustic solution residues, do not pass unrecognized through the testing apparatuses. With filled containers, the internal pressure must be not too high and not too low. Cans must be in a satisfactory state before filling and must be satisfactorily sealed after filling.

A procedure frequently used with empty-bottle inspectors when checking on the absence of foreign bodies in that an image of the object is scanned pointwise e.g. by means of a CCD camera, generally in two directions at right angles to each other, and the brightness of each image point is ascertained and light-dark and dark-light transitions recorded by comparison with the brightness of adjoining image points. Such a transition always occurs e.g. if the scan passes over the edge of a foreign body in an empty bottle. Even empty bottles which are free from foreign bodies have a certain number of brightness transitions, e.g. up to 100 brightness transitions, due to uneven zones in the receptacle wall or the fluting on the edge of the base. A single object counts in this case as free from foreign bodies up to 100 brightness transitions, i.e. a feature signal of 100 still satisfies the first condition.

During proper operation e.g. of an empty bottle inspector, a feature signal is obtained for the predominant majority of the empty bottles e.g. 90%, which is somewhat below the number of 100 light-dark transitions. If the sensitivity of the recognition device of the testing apparatus drops due to dirt or other reasons, this tends to lead to a decrease in the number of light-dark transitions recognised per empty bottle. Depending on how large the deviation from the reference value is, various measures can be taken. For a deviation of 10% e.g. a warning signal can simply be given out, while for a deviation of 20% or more the testing apparatus and the entire transport apparatus can be stopped.

A particularly advantageous version of the method according to the invention results in conjunction with defect recognition methods in which not only the number of light-dark transitions are counted, but also the light-dark contrast of the brightness transitions is established. The found image elements deviating from the background are divided into e.g. eight different brightness classes or the light-dark transitions are divided into e.g. eight different contrast groups, the number of light-dark transitions being counted only after this classification and being compared within each class with a special threshold value. If the recognition device of the testing apparatus is dirty, a light scatter appears on the lenses or the glass protection disks, which leads to a decrease in the light-dark contrast, as a misty-like blurring effect covers the image scanned by the recognition device because of the light scatter. The reduction in the light-dark contrast causes a shift in the light-dark transition within the contrast classes, in such a way that the feature signals more frequently fall in the classes with less contrast. When testing the reliability of the testing apparatus, there is now no need to rely just on the comparison of the number of light-dark transitions, but a comparison is carried out with a threshold value in every one of the contrast classes and, in addition, the distribution of the feature signals over the individual contrast classes can be taken into account.

Assuming that a test bottle free from defects has 100 light-dark transitions of the order of 250 shades of grey, and two contrast classes are used, the first contrast class containing light-dark transitions with under 180 shades of grey and the second contrast class containing light-dark transitions with over 180 shades of grey: if the lens system of the recognition device is slightly dirty, then 100 light-dark transitions are still recorded, but with diminished contrast, e.g. only 150 shades of grey. The established feature signal then reads "100 light-dark transitions in the second contrast class" and thus does not correspond to the reference value which reads "100 light-dark transitions in contrast class 1". The deterioration in the possibility of defect recognition by the recognition device thus becomes noticeable by shifting the light-dark transitions from contrast class 1 into contrast class 2. Through this version of the method according to the invention, statements can be made about the reliability of the recognition of in particular small defects or defects in the form of transparent foreign bodies.

With this version of the method according to the invention, the feature signal thus not only contains details of the number of light-dark transitions but also details of the distribution of the light-dark transitions over the different contrast classes. Corresponding details are also contained in the reference value. A particularly early recognition of the reduction in the sensitivity of the recognition device is thereby possible. A dirtying of the lens (system) of the recognition device does not lead firstly e.g. to change in the amount of light-dark transitions, but certainly leads to a change in the distribution of the light-dark transitions among the different contrast classes.

Empty-bottle inspecting devices furthermore check the roundness of the opening of empty bottles. The aim is to eliminate empty bottles in which the edge of the opening has splinters. For this, a radiation of light is directed onto the opening and the image which emerges from the reflection of this radiation is evaluated by means of a CCD camera. The image evaluation facility comprises an outer annular recognition zone which corresponds to the outward-dropping zone of the mouth, as well as an adjoining inner annular recognition zone which corresponds to the horizontal zone of the mouth. The splinter leads in the outer recognition zone to a decrease in the number of light-dark transitions, while it leads to an increase in the number of light-dark transitions in the inner recognition zone.

The recognition method in which the number and optionally the contrast of the light-dark transitions is determined, is suitable in particular for recognizing foreign bodies in empty bottles and for recognizing splinters in the mouth opening. Absorbent foreign bodies, e.g. dirt, are established by the bright-field method, while transparent foreign bodies, e.g. films, are detected by the dark-field method (EP-A-0 387 930). The individual zones of an empty bottle and in particular of the base of the bottle are examined separately. By the method according to the invention, the reliability of a testing apparatus can be tested separately for every type of defect and every recognition zone, as an individual reference value is entered or read in for every type of error and every recognition zone.

By means of the method according to the invention, the reliability of a testing apparatus which detects caustic solution residues in empty bottles can also be tested. Caustic solutions are polar liquids so that they conduct high-frequency electric radiation better than air. Caustic solution residues can therefore be recognized by ascertaining the absorption of high-frequency electromagnetic radiation. The feature signal is a measure of the lesser absorption of the electromagnetic radiation which it experiences through the caustic solution residues. If the intensity of the electromagnetic radiation let through by an empty bottle exceeds a threshold value, the first condition is no longer fulfilled and the empty bottle concerned is eliminated as defective from further production steps. The reference value which is entered in the testing apparatus corresponds to an empty bottle without caustic solution residues. When testing the reliability of the caustic solution residues testing apparatus, the test signal must correspond to the reference value with minor deviations. At the same time, the caustic solution residues test is an example of how the method according to the invention can also be used with analogue feature signals.

A further example is the determination of liquid remains on the base of the bottle by measuring the resulting attenuation of IR light. Caustic solution residues in an empty bottle are recognized both in the preceding special test for caustic solution residues and the general determination of liquid residues by means of IR attenuation. Certain features of objects can thus also be tested in two different ways.

The method according to the invention can also be used to test the reliability of testing apparatus which work with different initial variables as feature signal. Examples are systems for recognizing light or dark pixels or systems for evaluating brightness distributions, (histograms), which, considered for themselves or after evaluation via arithmetic algorithms, represent parameters for the quality of bottles or other objects.

In the simultaneously filed patent application entitled "Method for determining parameters, e.g. fill level, pressure or gas composition, in closed containers" (in-house reference: 31457/Fullstandsk., corresponds to DE 196 46 685.7), a method is described for determining the fill level of liquids in containers which are sealed by a cap, the cap being excited by a short magnetic pulse to perform primary mechanical vibrations. The secondary vibrations excited by the primary mechanical vibrations of the cap in the container, which take place within the space between the cap and the liquid, are recorded by means of a microphone and are analysed, the fill level being ascertained from the established frequency of these secondary vibrations. The internal pressure of the container can additionally be deduced from an analysis of the primary mechanical vibrations. The method according to the invention can also be used on this occasion. The feature signal is on this occasion the frequency of the secondary vibrations for the fill level. The first condition is that this frequency lies above a certain value, e.g. 7 kHz; smaller frequencies mean too large an air space in the neck of the bottle and thus too low a fill level. The second condition, which is characteristic for the correct operation of the testing apparatus, is that the test signal corresponds to the set reference value which was previously entered.

A further possible way of testing the reliability of a testing apparatus and in particular the cleanness of the optical recognition system results when checking the wall contrast during side wall recognition. The contrast difference, i.e. the brightness difference of the edge of the bottle, which appears black due to the strong refraction of the light radiation penetrating it, is determined in relation to the background lighting or to the brightness of the centre of the bottle. Deviations from the average of this brightness difference allow a very early statement about a deterioration in recognition efficiency and thus in the reliability of the testing apparatus.

The sensitivity of the testing apparatus can be automatically tracked in a certain zone by means of the previously described versions of the method according to the invention. If certain limit values are exceeded, a warning signal is then emitted, and if a further limit value is exceeded, the testing apparatus can then be stopped, as there is no longer certainty of recognition of specific defects.

What is claimed is:

1. A method for testing the reliability of a testing apparatus which checks multiple objects of the same type for one set feature, the method comprising the steps of: generating a feature signal for each object; checking the feature signal for fulfillment of a first condition; deriving a test signal from the feature signals of a plurality of objects of a common type; and checking the test signal for fulfillment of a second condition in order to test the reliability of the testing apparatus, wherein the step of checking the test signal includes comparing the test signal with a reference value, and wherein the test signal is an average of the feature signals of several objects, the reference value is a value of the feature signal to be expected for defect-free objects, and wherein a permitted deviation of the test signal from the reference value (second condition) is smaller than a deviation at which the first condition is fulfilled for an individual object.

2. The method according to claim 1, wherein during averaging, feature signals which do not fulfill the first condition are not taken into account.

3. The method claim 1 wherein the objects are containers which are made of transparent material, in which the testing apparatus serves to recognize foreign bodies in the containers and has a light source and a recognition apparatus, further comprising the steps of: scanning an image of the relevant container pointwise by the recognition apparatus, determining a brightness of each image point and establishing light-dark and dark-light transitions by comparing the brightness of neighboring image points, using the number of established light-dark and dark-light transitions as a criterion for the presence of foreign bodies and as the feature signal, and comparing the feature signal with a threshold value, the first condition being that the feature signal does not exceed the threshold value, wherein the test signal is the average of the feature signals of several objects and that the second condition is that the test signal deviates upward or downward from the reference value by about 5%.

4. The method according to claim 3, further comprising the steps of: establishing a brightness difference of individual light-dark and dark-light transitions, and dividing the established light-dark and dark-light transitions into a plurality of contrast classes according to the established brightness difference, wherein the distribution of the light-dark and dark-light transitions over the contrast classes are contained in the feature signal and the test signal and wherein when the second condition is checked, this distribution is taken into account.

5. The method according to claim 4, wherein the sensitivity of the recognition apparatus is tracked according to the contrast measured.

* * * * *